US00PP34437P2

(12) United States Plant Patent
Dodd et al.

(10) Patent No.: US PP34,437 P2
(45) Date of Patent: Jul. 26, 2022

(54) APPLE TREE NAMED 'MAIA-SM'

(50) Latin Name: ***Malus* x *domestica***
Varietal Denomination: 'MAIA-SM'

(71) Applicants: William Dodd, Amherst, OH (US); David Doud, Wabash, IN (US); John Mitchel Lynd, Pataskala, OH (US); Gregory Miller, Carrollton, OH (US)

(72) Inventors: William Dodd, Amherst, OH (US); David Doud, Wabash, IN (US); John Mitchel Lynd, Pataskala, OH (US); Gregory Miller, Carrollton, OH (US)

( * ) Notice: Subject to any disclaimer, the term of this patent is extended or adjusted under 35 U.S.C. 154(b) by 0 days.

(21) Appl. No.: 17/218,733

(22) Filed: Mar. 31, 2021

(51) Int. Cl.
*A01H 5/08* (2018.01)
*A01H 6/74* (2018.01)

(52) U.S. Cl.
USPC ..... Plt./161

(58) Field of Classification Search
USPC ..... Plt./156, 161
See application file for complete search history.

(56) References Cited

U.S. PATENT DOCUMENTS

PP20,437 P2 * 10/2009 Korban ..... A01H 6/7418 Plt./161

* cited by examiner

*Primary Examiner* — Karen M Redden
(74) *Attorney, Agent, or Firm* — Timothy Simmons

(57) ABSTRACT

A new and distinct variety of apple was identified from a population of seedlings derived from a controlled cross of 'Honeycrisp' and 'Co-op 31.' The new variety, named 'MAIA-SM' ripens in late August. 'MAIA-SM' has distinctly different skin color than its parent varieties in lenticel appearance and ground color. 'MAIA-SM' has consistent annual cropping with minimal horticultural inputs and achieves a full sweet flavor earlier than most apple varieties. 'MAIA-SM' is the apple most preferred by consumers in a blind taste test during the apple harvest window before 'Honeycrisp.'

3 Drawing Sheets

Latin name: Latin name of the genus and species of the plant claimed: *Malus* x *domestica.*

Variety denomination: Variety denomination: 'MAIA-SM'.

BACKGROUND OF THE INVENTION

A new and distinct variety of apple was identified from a population of seedlings derived from a controlled cross of 'Honeycrisp' (U.S. Plant Pat. No. 7,197) and 'Co-op 31' (WineCrisp™; U.S. Plant Pat. No. 20,437). This cross was made as a part of an apple breeding project. This seedling tree was identified from a population of seedlings near Wabash, Ind.

The seedling tree was planted as a 1-year-old tree near Wabash, Ind. in 2001 and grown among a population of several hundred siblings. Evaluations of fruit quality and tree growth parameters were begun in 2005 and this seedling was identified over several years as superior based upon tree growth habit, precocity, superior fruit quality, and harvest time. Utilizing grafting reproduction, the new apple tree variety was asexually propagated in 2010 near Wabash, Ind. and has been observed to remain true to the description set forth herein, through successive generations. While T-budding was used initially to reproduce the new apple tree variety, it is expected that other industry recognized grafting methods would be effective.

The new variety, named 'MAIA-SM' is distinct from 'Honeycrisp' as 'MAIA-SM' ripens in late August, 1-2 weeks before 'Honeycrisp' (FIG. 1). The fruit of 'MAIA-SM' has fully red skin (Greyed-Purple 185A) unlike the characteristic two-tone skin color of Honeycrisp. 'MAIA-SM' is distinct from 'Co-op 31' in that it ripens in late August, 6-7 weeks before 'Co-op 31.' 'MAIA-SM' and 'Co-op 31' have similar skin color; however, 'Co-op 31' has more prominent lenticels and a greener ground color in comparison to the inconspicuous lenticels and orange ground color (Greyed-Orange N163A) of 'MAIA-SM.' Although the parent varieties are the most closely related commercial varieties to 'MAIA-SM' as it is the only known commercially viable variety derived from a cross of 'Honeycrisp' and 'Winecrisp,' 'MAIA-SM' is also distinct from another 'Honeycrisp' derivative known as 'Cosmic Crisp' (also known as 'WA 38,' U.S. Plant Pat. No. 24,210) in that 'MAIA-SM' ripens in late August, 5-6 weeks earlier than 'WA 38' and that 'MAIA-SM' lacks the prominent lenticels of 'WA 38.' 'MAIA-SM' fruit are medium sized, crisp, firm, with a pleasant fully sweet flavor preferred by consumers in blind taste tests.

BRIEF DESCRIPTION OF THE DRAWINGS

The accompanying photographs show typical specimens of the new variety as depicted in color as nearly true as is reasonably possible. 'MAIA-SM' photographs were taken near Wabash, Ind.

DETAILED BOTANICAL DESCRIPTION

Figure 1:
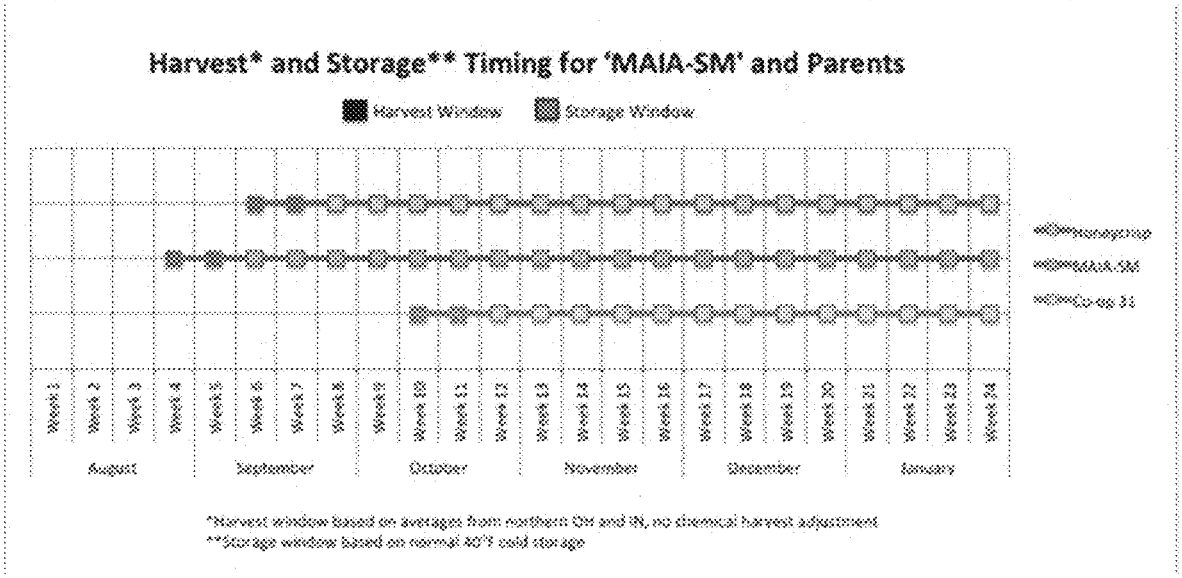
FIG. 1. Shows that 'MAIA-SM' is distinct from 'Honeycrisp' and 'Co-op 31' in harvest window. Harvest data is from Wabash, Ind.
Figure 2:
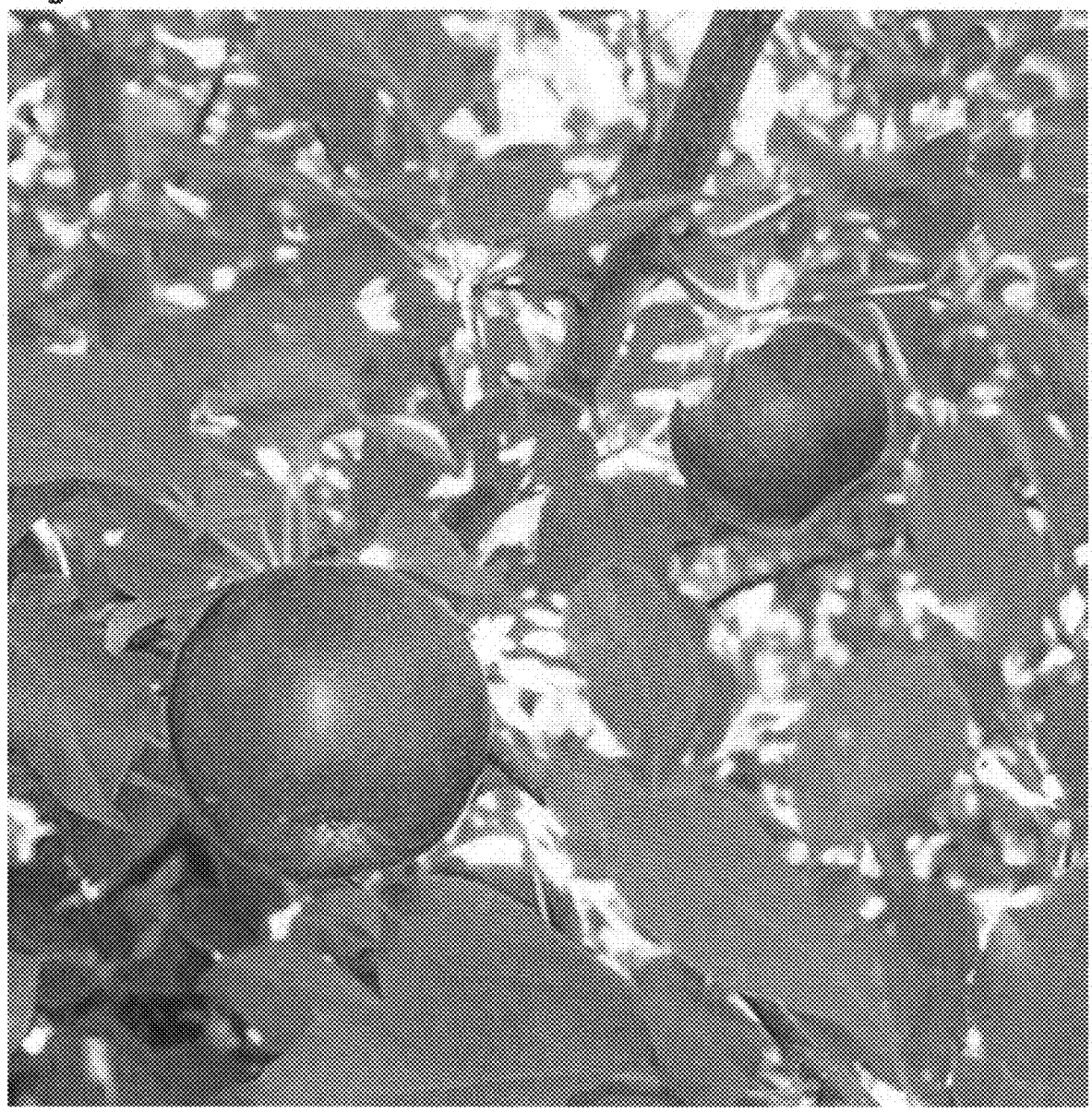
FIG. 2. Typical fruit of 'MAIA-SM' at harvest time on an eight-year-old tree.
Figure 3:
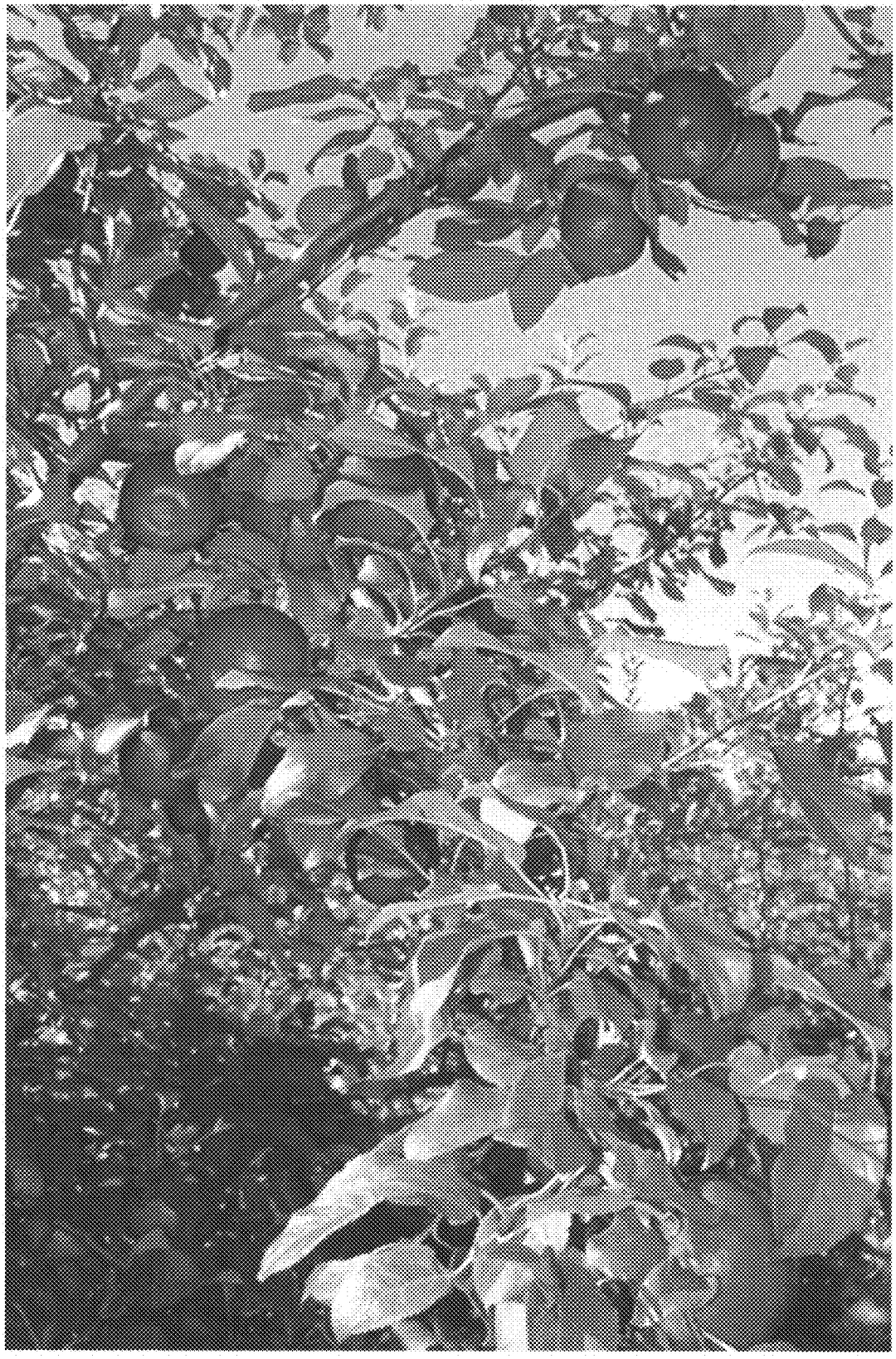
FIG. 3. Typical 'MAIA-SM' fruiting habit on the eight-year-old ortet tree in Indiana.

Color references are made to The Royal Horticultural Society Colour Chart (R.H.S.) 2001 Edition.

Parentage: 'Honeycrisp' female parent and 'Co-op 31' (WineCrisp™) male parent; cross made by Mitch Lynd at Pataskala, Ohio in 1999.

Grafted tree on B9 rootstock (unpatented, reference tree):
- *Age.*—12 years.
- *Size.*—10' height, 6' spread.
- *Vigor.*—Moderate.
- *Form.*—Round, spreading.
- *Production.*—Very productive (700 bushels per acre, on average).
- *Growth type.*—Spindle tree growth form, productive spurs located throughout tree.
- *Bearing.*—Annual.

Trunk:
- *Reference tree diameter.*—5 cm at 12 cm height.
- *Bark color.*—Greyed-Orange 177B.
- *Lenticels.*—Oblong, 3×1 mm.
- *Lenticel color.*—Orange-White 157B.
- *Lenticel density.*—5-10 lenticels/cm$^2$.

Branches:
- 3 *year old.*—10-13 mm in diameter, branch angle 85°; Greyed-Orange 177B.
- 2 *year old.*—6-8 mm in diameter, branch angle 90°; Greyed-Orange 177B.
- 1 *year old.*—3 mm in diameter, branch angle 80°; Grey Group 201C.

Leaves:
- *Size.*—Length 65-85 mm; width 35-44 mm.
- *Texture.*—Leathery, crisp.
- *Form.*—Ovate.
- *Base.*—Roundly cuneate.
- *Apex.*—Acute.
- *Adaxial surface pubescence.*—None.
- *Abaxial pubescence.*—Finely pubescent.
- *Adaxial surface color.*—Green Group N137A.
- *Abaxial surface color.*—Yellow-Green 147C.
- *Venation.*—Pinnate, 6-9 major veins, mainly alternate; Greyed-Red 182B.
- *Margin.*—Serrate.
- *Petiole length.*—20-30 mm.
- *Petiole width.*—2-3 mm.
- *Petiole abaxial color.*—Greyed-Purple 185A.
- *Petiole groove.*—Very shallow, depth 0.1 mm.
- *Stipules.*—Present; 7 mm length; 2 mm width; Green Group N137B.
- *Leaf glands.*—None observed.

Leaf buds:
- *Length.*—5-6 mm.
- *Width.*—3 mm.
- *Color.*—Greyed-Purple 187A.
- *Placement on branch.*—Alternate.
- *Internode distance.*—15-30 mm.

Spurs: Present on 2 yr and older wood.
- *Length.*—Varies from 20 to 100 mm.
- *Width.*—5-8 mm.

Flowers at popcorn stage:
- *Pedicel.*—Length 21-32 mm; width 2-2.5 mm.
- *Pedicel color.*—Greyed-Green 194B.
- *Bud.*—Length 7 mm; width 6 mm.
- *Bud color.*—Red Group 38C.

Flowers at full bloom:
- *Bloom time.*—Blooms with 'Golden Delicious' Bloom time varies with temperature, but is typically during the 4th week of April in northern Indiana.
- *Bloom period.*—Approximately 7 days.
- *Presentation.*—Very Showy.
- *Fragrance.*—Aromatic.
- *Fertility.*—Fertile.
- *Number of flowers per cluster.*—4-6 with 5 typical.

Petals:
- *Arrangement.*—Bases not overlapping; 5 petals per flower; each petal 19-23 mm length, 11-18 mm width.
- *Color.*—Upper surface (inside) White Group NN155C; Lower surface (outside) slightly colored, White Group N155C with Red Group 38C.
- *Shape.*—Broadly ovate, abruptly cuneate at junction with receptacle.
- *Veins.*—Distinct.
- *Margins.*—Mostly smooth and wavy, some notching.
- *Texture.*—Soft.
- *Receptacle.*—Length 4 mm; width 4 mm; color Greyed-Purple 196D; extremely pubescent.
- *Sepals.*—5/flower; wedge-shaped, sharply pointed; length 8-9 mm; width 4 mm at widest point; color Green Group 141C.
- *Stamens.*—18-20 in number.
- *Anthers.*—Length 2 mm; width 1.5 mm; color Yellow-Orange 22B.
- *Pollen.*—Present; color Yellow Group 10C.
- *Filaments.*—Length 6-9 mm; width 0.5 mm; color Green-White 157C.
- *Stigma.*—Held above the anthers in majority of blossoms.
- *Ovary.*—Length 3 mm; width 3 mm; color Green Group 143A.
- *Style.*—Length 10-11 mm; styles are fused in bottom 2 mm only; width 0.5 mm; color Yellow-Green 149B.
- *Stigma.*—Width 0.5 mm; color Yellow-Green 151A.

Pollination requirements: Requires cross-pollination from diploid varieties with overlapping bloom; will pollinate diploid varieties of overlapping bloom.

Fruit:
- *Maturity when described.*—2 month storage.
- *Date of picking:* 17 Aug. 2019.
- *Size.*—Axial diameter 68-75 mm; Transverse diameter shortest point 27-35 mm; Transverse diameter longest point 59-60 mm.
- *Fruit weight.*—152-190 g; average 173 g.
- *Form.*—Round, regular, symmetrical.
- *Cavity.*—Acute, medium deep, ground color extends out of cavity.
- *Basin.*—Medium depth, narrow, symmetrical, regular, ridged.
- *Calyx.*—Closed, reflexed, medium size.

Skin:
- *Thickness.*—Thin.
- *Tendency to crack.*—None.
- *Stripes.*—Partial, thin.
- *Lenticels.*—Round shape, very small, inconspicuous.
- *Color.*—Greyed-Purple 185A.
- *Ground color.*—Greyed-Orange N163A.

Flesh:
- *Aroma.*—Sweet, very aromatic.
- *Color.*—Yellow-Orange 18D.
- *Texture.*—Crisp, firm, fine, juicy.
- *Eating quality.*—Excellent.
- *Flavor.*—Sweet, rich, floral.

Core: Medium size.
- *Bundle area.*—728 mm$^2$.
- *Bundle.*—Inconspicuous.
- *Axial carpel length.*—11 mm.
- *Seed cells.*—Walls thin, tough.

Seeds:

*Number perfect.*—10.

*Number in one cell.*—2.

*Length.*—7-10 mm.

*Breadth.*—4-5 mm.

*Color.*—Brown Group 200B.

Stem:

*Length.*—20-25 mm.

*Width.*—3-4 mm.

*Color.*—Yellow-Orange 18A.

Use: Fresh market, dessert.

Shipping quality: Good.

Keeping quality: Excellent.

Drought tolerance: Average for domestic apple.

Tree winter hardiness: Average for domestic apple.

Disease:

*Resistance.*—Partial resistance to fireblight (*Erwinia amylovora*), apple scab (*Venturia inaequalis*), and powdery mildew (*Podosphaera leucotricha*).

*Susceptibility.*—Presumably susceptible to other fungal diseases common to *Malus* x *domestica.*

What is claimed is:

1. A new, distinct apple tree variety named 'MAIA-SM', as illustrated and described herein.

* * * * *